(12) United States Patent
Moss

(10) Patent No.: US 6,447,472 B1
(45) Date of Patent: Sep. 10, 2002

(54) METHOD AND PUMP APPARATUS FOR COMBINED GASTRO-INTESTINAL FEEDING AND ASPIRATION

(76) Inventor: Gerald Moss, 4049 NY 150, W. Sand Lake, NY (US) 12196

( * ) Notice: Subject to any disclaimer, the term of this patent is extended or adjusted under 35 U.S.C. 154(b) by 180 days.

(21) Appl. No.: 09/692,566

(22) Filed: Oct. 19, 2000

(51) Int. Cl.$^7$ ................................. A61M 1/00
(52) U.S. Cl. .................. 604/27; 604/264; 604/910; 604/500
(58) Field of Search ............ 604/910, 96, 500, 604/506, 93.01, 27, 35, 99.04, 264, 523, 317

(56) References Cited

U.S. PATENT DOCUMENTS

| | | | |
|---|---|---|---|
| 4,249,535 A | 2/1981 | Hargest, III | 128/348 |
| 4,300,550 A | 11/1981 | Gandi et al. | 128/207.18 |
| 4,676,778 A | 6/1987 | Nelson, Jr. | 604/45 |
| 5,071,405 A | 12/1991 | Piontek et al. | 604/96 |
| 5,098,378 A | 3/1992 | Piontek et al. | 604/49 |
| 5,203,769 A | 4/1993 | Clement et al. | 604/32 |
| 5,520,662 A | * 5/1996 | Moss | 604/246 |
| 5,573,504 A | 11/1996 | Dorsey, III | 604/35 |
| 5,665,064 A | 9/1997 | Bodicky et al. | 604/54 |
| 5,788,631 A | 8/1998 | Fiddian-Green | 600/309 |
| 5,832,920 A | 11/1998 | Field | 128/207.14 |
| 5,968,008 A | 10/1999 | Grams | 604/35 |

* cited by examiner

*Primary Examiner*—Edward K. Look
*Assistant Examiner*—Kimya N McCoy
(74) *Attorney, Agent, or Firm*—Schmeiser, Olsen & Watts

(57) ABSTRACT

In accordance with the present invention, a pump apparatus for use in conjunction with the feeding and aspiration of a patient's gastro-intestinal tract is provided. In accordance with the present invention, an apparatus and method are provided in which the aspiration of excessive material and air from a patient's gastro-intestinal tract proceeds until the flow of aspirate ceases. A flow detector determines when aspirate flow has ceased. Aspirate removed from the gastro-intestinal tract is retained for subsequent return to the patient for absorption to prevent dehydration. After the aspiration is concluded, material aspirated from the intestine and additional nutrition or fluids are introduced into the gastro-intestinal tract for absorption by the intestine. After an optional delay to allow for the absorption of materials by the intestine, the aspiration cycle resumes. This frequent aspiration serves to prevent overfeeding and its associated risks of intestinal distention.

16 Claims, 4 Drawing Sheets

METHOD AND PUMP APPARATUS FOR COMBINED GASTRO-INTESTINAL FEEDING AND ASPIRATION

BACKGROUND OF THE INVENTION

1. Field of the Invention

The present invention relates to a pump apparatus used to aspirate a patient's gastro-intestinal tract and/or to deliver nutrients, fluids, medication and/or aspirate into a patient's gastro-intestinal tract, preferably in conjunction with a combination feeding and aspiration tube. More specifically, this invention concerns a method and apparatus for use in cyclically or simultaneously aspirating, monitoring, and safely delivering nutrients, fluids, medications and/or aspirate into the gastro-intestinal tract as part of aspiration and feeding processes, permanently removing only potentially deleterious, physiologically excessive fluids.

2. Description of the Prior Art

Nutrients, fluids, medications and/or aspirate (collectively referred to as "feedings") often are introduced directly into a patient's gastro-intestinal tract via a feeding tube. This situation is discussed more fully in U.S. patent Application entitled "Single Lumen Gastro-Intestinal Feeding-Decompression Tube", filed herewith.

In many cases, a patient's intestine is not operating fully, limiting the amount of nutrition the patient may receive. However, adequate nutrition is obviously a critical part of anyone's health and is necessary to provide optimum recovery for a patient. It is thus desirable to deliver as much nutrition to a patient as can be absorbed safely by the patient's impaired gastro-intestinal tract.

Unfortunately, it is not desirable simply to deliver a maximum amount of nutrition into a patient's intestine. The reason for this is that overfeeding, which is delivering feedings at a rate exceeding the ability of the patient's gastro-intestinal tract to absorb its own secretions plus the added nutrition, itself presents serious hazards to a patient. Overfeeding a patient leads to an accumulation of fluid, which distends the intestine. This intestinal distension can lead to fatal circulatory changes. More commonly, complications from overfeeding include the temporary further impairment of intestinal function, with nausea and vomiting, which at a minimum causes discomfort and delays recovery. Accordingly, it is desirable to limit delivery to avoid overfeeding, while at the same time delivering into the impaired intestine the maximum nutrition that can be absorbed safely.

Further complicating the feeding of patients via feeding tube is the fact that the body of its own accord produces considerable digestive secretions on a regular basis. In a healthy person, all of these digestive secretions, starting with saliva, are re-absorbed by the intestine, leading to no net change in bodily fluids. During a patient's recovery from surgery or illness, the creation of digestive secretions is typically unaffected. Unfortunately, a patient's gastro-intestinal function may be impaired considerably during recovery, so that the re-absorption of digestive secretions may not fully occur. Thus, nutrition delivered to the intestine may be competing with digestive secretions for absorption by the intestine. Furthermore, the presence of a feeding tube induces swallowing by a patient, which introduces additional air into the gastrointestinal tract. Swallowed air further compromises absorption. Meanwhile, it is not desirable to simply remove digestive secretions from a patient's system, as this will dehydrate the patient. For this reason, feedings should be delivered to the patient in a way that accounts for any possible excess of digestive secretions, without dehydrating the patient, while also minimizing the presence of air.

Previously, a feeding tube might be aspirated manually to "check for residual" as a safety measure. In this process, feeding is interrupted and that portion of the patient's gastro-intestinal tract is manually aspirated via the feeding tube. This "residual" volume is measured and compared with an expected volume for an individual with normal gastro-intestinal function to determine whether the feeding rate should be maintained, increased, or reduced. The aspirate is either re-introduced or discarded. However, the check for residual process is labor intensive and, therefore, seldom used. Also, the check for residual process can, as a practical matter, be performed only a few times per day, which does not monitor gastro-intestinal function as closely as desired when directly feeding into the intestine.

As a step towards resolving these feeding difficulties, the inventor named herein has conceived of a single lumen gastro-intestinal feeding-decompression tube for use in delivering nutrition to a patient's intestine and in net fashion removing all air and any excess liquids that are present in the intestine. This feeding tube is disclosed more fully in a U.S. patent application entitled "Single Lumen Gastro-Intestinal Feeding-Decompression Tube", filed simultaneously herewith. This application focuses upon a method and a pump control apparatus for use with the method for cyclically or simultaneously aspirating, monitoring, and delivering nutrition into the gastro-intestinal tract as part of aspiration and feeding processes. The pump control apparatus in accordance with the present invention may be used in conjunction with the applicant's single lumen gastro-intestinal Feeding-decompression tube, as well as other feeding tubes that may be used in the simultaneous delivery of nutrition and aspiration of a patient's gastro-intestinal tract. An alternative embodiment of the present invention provides simultaneous feeding and aspiration of the gastro-intestinal tract with separate feeding and aspiration tubes.

SUMMARY OF INVENTION

The present invention comprises a method and pump control assembly for use in alternating the delivery of nutrition to a patient's gastro-intestinal tract and aspirating air and/or excess fluid from the gastro-intestinal tract. In its preferred embodiment, the pump assembly includes a relatively dense ball and a detector to sense the position of the ball. The position of the ball controls the operation of the pump. The relatively dense ball is lifted while material is being aspirated from the gastro-intestinal tract, but drops when the flow of aspirate stops. When the ball drops, the aspiration cycle is terminated and a feeding cycle begins.

In its broader sense, the pump control apparatus comprises a flow detector that controls the delivery of nutrition to and aspiration from a patient's gastro-intestinal tract based upon the amount of aspirate flow obtained from a patient's gastro-intestinal tract. Aspiration continues until aspirate flow ceases. After the aspirate flow ceases, a feeding cycle may commence. After the feeding cycle, the aspiration may resume.

The invention further comprises a method of delivering nutrition to a patient's gastro-intestinal tract and aspirating the gastro-intestinal tract so as to obtain maximum nutritional absorption by the gastro-intestinal tract without the risk of overfeeding.

BRIEF DESCRIPTION OF DRAWINGS

The invention may be better understood by reference to the drawings in which.

It should be appreciated that these drawings are for illustrative purposes and are not necessarily to scale.

DETAILED DESCRIPTION OF THE PREFERRED EMBODIMENT

The preferred embodiment and an alternative embodiment of the present invention are illustrated in reference to the figures. A pump apparatus in accordance with the present invention alternates cycles of aspiration and feeding when used in conjunction with appropriate feeding and/or aspiration tube(s). During the aspiration phase, material such as air, digestive secretions, and excessive nutrition are removed from the patient's intestine. After the aspiration phase is concluded, normal, tolerable quantities of removed bodily fluids plus added nutrition are delivered to the intestine.

Figure 1:
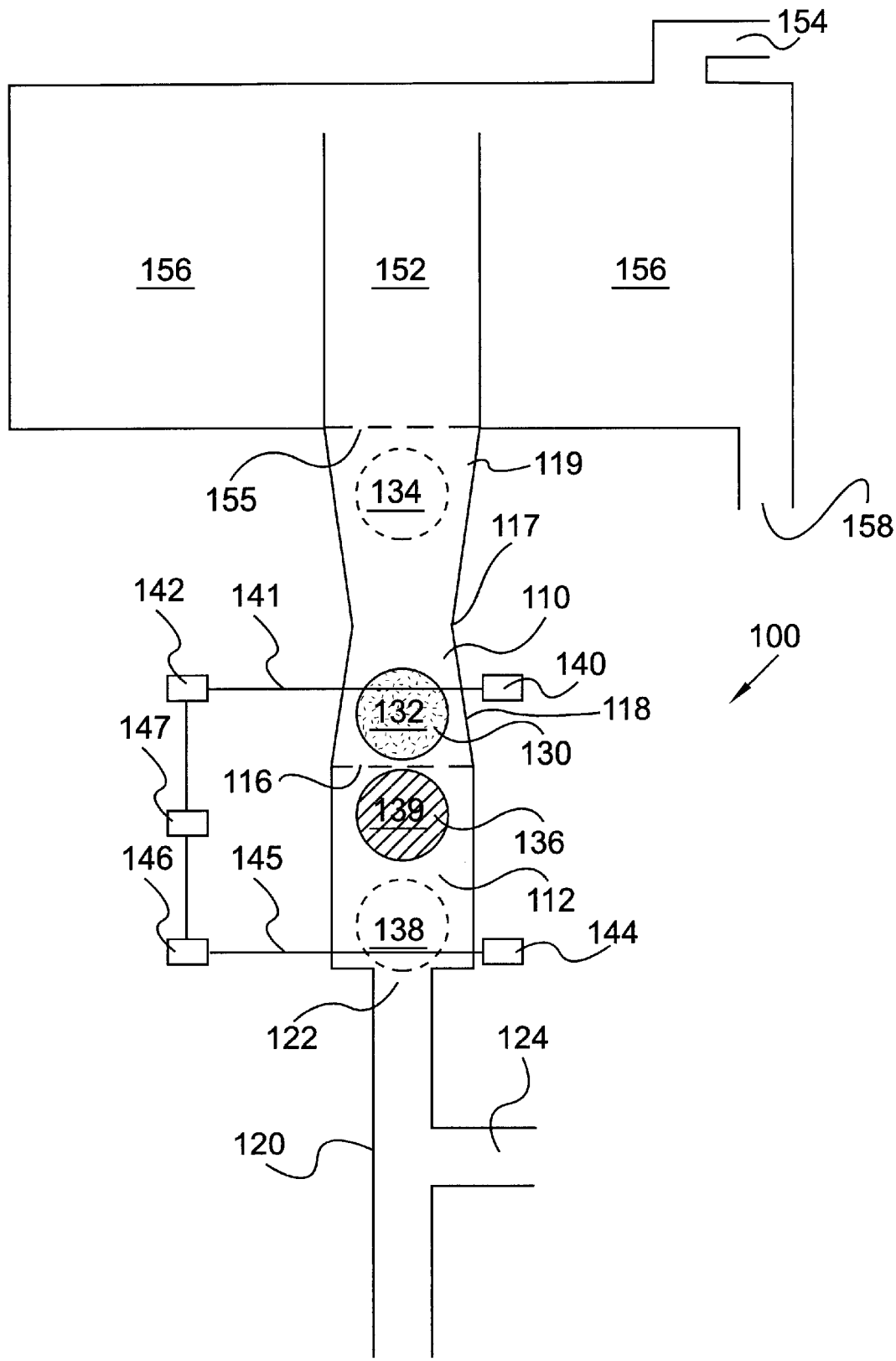
FIG. 1 is a schematic diagram of a pump control apparatus in conjunction with the preferred embodiment of the invention.

After an appropriate amount of time for feedings to be propelled along the intestine by peristalsis, the aspiration phase resumes, again removing potentially excessive nutrition and other materials. Only air and potentially deleterious, physiologically excessive fluids are removed permanently. FIG. 1 illustrates a pump control apparatus in accordance with the preferred embodiment of the present invention. The pump control apparatus 100 includes an upper chamber 110 and a lower chamber 112. The upper chamber 110 is substantially hour glass shaped, having a lower portion 118 and an upper portion 119, with a restrictive middle portion 117. A lower chamber 112 is located below the upper chamber 110. Channels 116 operably connect the upper chamber 110 and the lower chamber 112 and allow material to pass freely between the lower chamber 112 and the upper chamber 110. Material aspirated from the gastro-intestinal tract flows through tubing 120 and into the lower chamber 112 through orifice 122. Orifice 122 may be characterized as a connection point between the pump control apparatus 100 and the pump (not shown). The reversible, variable rate pump (not shown) is connected to the feeding and aspiration tube (not shown). Aspirated material then flows through the channels 116 into the upper chamber 110. Aspirated material flows from the upper chamber 110 and through opening 155 into a fixed volume (for example, 10 ml) burette 152. Excess material overflows from the fixed volume burette 152 into a holding container 156 for disposal or manual return to the patient's gastro-intestinal tract. Air is vented from the aspirate and exits at vent 154.

Material is aspirated from the gastro-intestinal tract using an appropriate pump, such as a reversible, variable rate Roller Pump (not shown). The Roller Pump is operably connected to the connection point 122 and moves aspirated material from the gastro-intestinal tract to the lower chamber 112 via the tubing 120. Preferably, the tubing 120 connects to a single lumen jejunal feeding-decompression tube, as more fully described in U.S. Patent Application entitled "Single Lumen Gastro-Intestinal Feeding-Decompression Tube." Tubing 124 transmits nutrition from a nutrition source (not shown) to tubing 120 for delivery into the intestine. A non-occlusive heavy ball 130 is contained in a free floating manner within upper chamber 110. When no aspirate flow passes through upper chamber 110, the non-occlusive heavy ball 130 drops to the lower portion 118 of upper chamber 110 to position 132. When aspirate flows through upper chamber 110 the non-occlusive heavy ball 130 is lifted above the hour glass restriction 117, and supported by even a relatively sluggish flow within the upper portion 119 of upper chamber 110 to position 134.

A light opaque ball 136 is positioned in a free floating manner so as to float in any liquid present within the lower chamber 112 in position 139. When all liquid has exited from the burette 152 and the upper chamber 110, the liquid level falls within the lower chamber 112. The ball 136 progressively drops, and may reach its lowest possible position 138, where it occlusively seats itself in opening 122 at the bottom of lower chamber 112.

When use of the pump control apparatus 100 is initiated, power is delivered to the Roller Pump (not shown) to initiate aspiration for a minimum amount of time, such as ten seconds. A light source 140, located outside of the upper chamber 110, transmits a beam of light along line 141 across the upper chamber 110 to be received by photocell 142. A brisk flow of aspirate may be expected initially, which causes the heavy non-occlusive ball 130 to rise from the lower portion 118 of the upper chamber 110, where it continues to be supported above the restriction 117 by even minimal flow. Failure of the ball 130 to rise at all during the initial ten seconds prevents photocell 142 from receiving light from light source 140 during that time which activates an alarm (not shown). The aspiration phase continues after the initial ten seconds only as long as the photocell 142 continues to be activated by light.

When aspiration flow completely ceases, the heavy non-occlusive ball 130 drops to the lower portion 118 of the upper chamber 110 to position 132, and the light beam along line 141 is interrupted, causing photocell 142 to no longer receive light from light source 140. When the light beam received by photocell 142 is interrupted by the nonocclusive ball 130, this indicates that no further aspirate flow is passing through the upper chamber 110. Accordingly, a switching mechanism 147 causes the Roller Pump (not shown) to cease aspirating the intestine, ending the aspiration phase.

As can be seen from the above description, the upper chamber 110, heavy nonocclusive ball 130, light source 140, and photocell 142 comprise a flow detector, which is used to detect a flow of aspirated material. Aspiration continues, after its initial start, only as long as a flow of aspirate is detected by the flow detector. One skilled in the art will realize that innumerable flow detectors may be used in conjunction with the present invention other than the flow detector described herein.

A second light source 144 is positioned outside of the lower chamber 112. The second light source 144 transmits a beam of light along line 145 through the lower chamber 112. Across the lower chamber 112 from the light source 144 is a second photo cell 148 positioned so as to receive the light beam transmitted along line 145. When liquid fills the lower chamber 112, the light opaque ball 136 floats within the lower chamber 112 to position 139. After all liquid has exited the fixed volume burette 152 and the upper chamber 110, the liquid level in the lower chamber 112 falls. The floating ball 136 descends within lower chamber 112, thereby interrupting the transmission of light along line 145 from the second light source 144 to the second photo cell 148. The interruption of the transmission of light and its receipt by the second photo cell 148 essentially indicates that all material removed during the previous aspiration cycle and retained within the burette 152 and the pump control apparatus 100 has been returned to the patient via the tubing 120. Accordingly, whenever the ball 138 interrupts the transmission of light received by photocell 148, the switching mechanism 147 causes the Roller Pump (not shown) to cease to return previously aspirated material to the patient's gastro-intestinal tract. It is to be observed that the occlusive seating of the ball 136 within the connection point 122 at position 138 assures that no air will be introduced to the patient's gastro-intestinal tract via the tubing 120 should the Roller Pump, switching mechanism 147, or the photo cell 148 fail to function properly and cause inappropriate continued delivery.

As material is aspirated from the patient, it is moved through upper chamber 110 to a reservoir 152. The reservoir 152 may appropriately comprise a 10 ml burette, although other sizes may be used. Any air within the aspirate freely escapes. The 10 ml reservoir 152 holds up to 10 ml of fluids that have been aspirated from the patient that will subsequently be returned to the patient's gastro-intestinal tract. Should more than 10 ml of aspirate be removed from the patient's gastro-intestinal tract, which may occur if a patient's intestinal function is severely impaired, the excess material will overflow from the 10 ml reservoir 152 to an overflow chamber 156. The overflow chamber 156 may appropriately be a 1000 ml chamber designed to retain excess aspirate. The excess aspirate may appropriately be removed from the overflow chamber 156 via a channel 158. The volume of any excess aspirate that overflows into the overflow chamber 156 must be appropriately recorded by the hospital staff. Ultimately, a volume of fluid equal to the excess aspirate must be returned to the patient to prevent dehydration. It is to be noted that during normal operation it is anticipated that virtually all fluids aspirated from the patient may be accommodated temporarily within the 10 ml reservoir 152 and ultimately returned to the patient to be reabsorbed. Any air in the aspirate is vented at vent 154.

Figure 2:
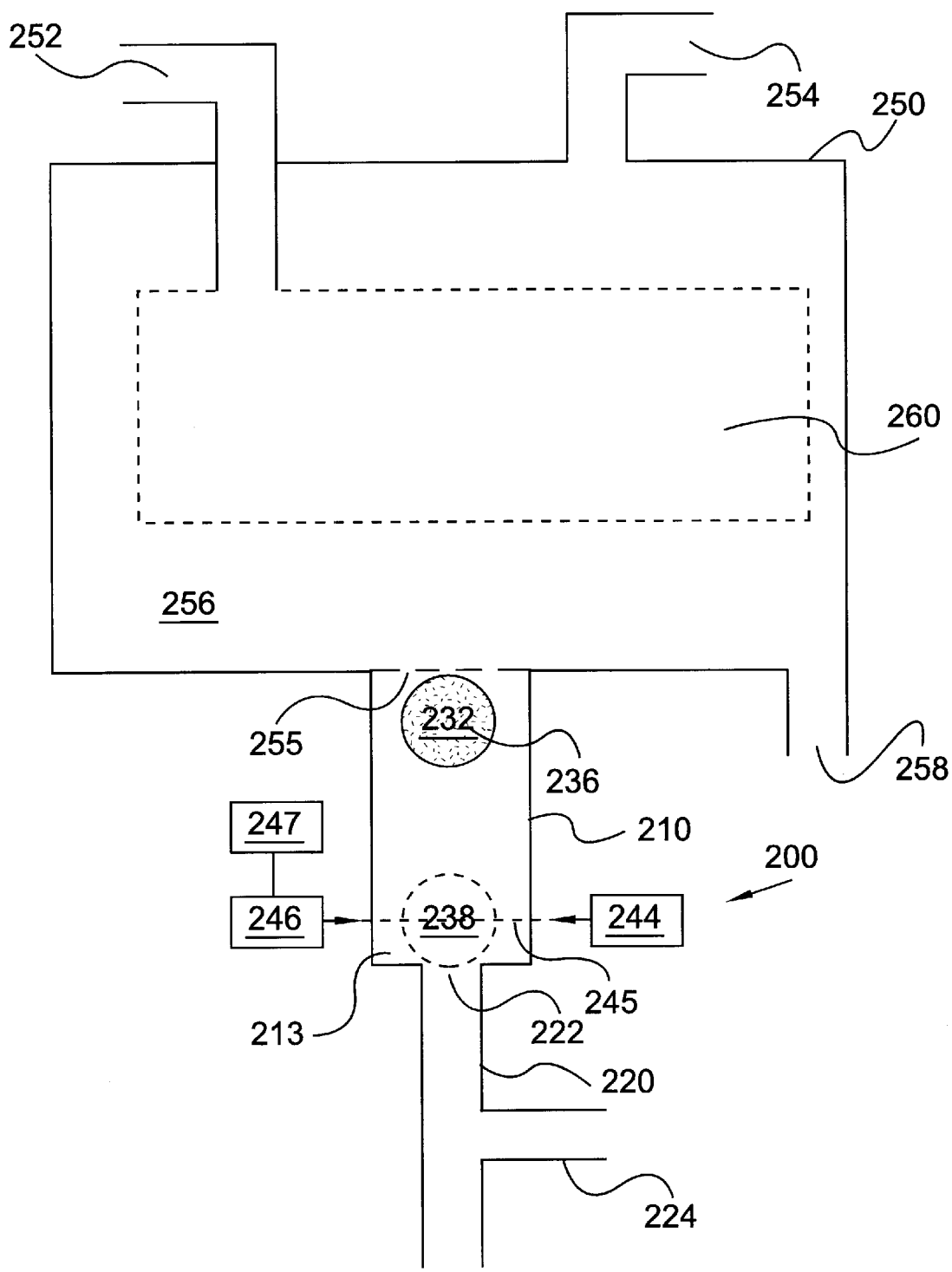
FIG. 2 is a schematic drawing of an alternative embodiment of a pump control apparatus in accordance with the present invention.

Referring now to FIG. 2, an alternative embodiment of a pump control apparatus 200 is illustrated. The alternative embodiment of the pump control apparatus 200 illustrated in FIG. 2 is particularly adapted for use with tubes other than the single lumen feeding tube ideally used with the preferred embodiment of the invention disclosed in FIG. 1. Specifically, the pump control apparatus 200 illustrated in FIG. 2 is adapted for use in simultaneous aspiration and delivery of nutrition, fluids, medicine and/or aspirate via two separate tubes, one for aspiration and one for delivery of feedings, or via a double lumen tube, wherein one lumen provides feedings and a second lumen performs the aspiration function. This pump control apparatus 200 includes a single chamber 212 and a single light occlusive ball 236. The ball 236 is positioned in a free floating manner within the chamber 212 so that it floats at position 232 when liquid material is present within the chamber 210. Aspirate is received into reservoir 256 from an aspiration tube (not shown) via tubing 252. Air is vented from the aspirate at vent 254. Solids are removed from the aspirate by the filter 260. Filtered aspirate flows from reservoir 256 through channels 255 into the chamber 210. The aspirate is returned to the patient via tubing 220 using a Roller Pump (not shown) operatively connected to the connection point 222.

A light source 244 is positioned outside of the chamber 212 so as to transmit light across the chamber 212 along line 245. A photocell 248 is positioned across the chamber 212 from the light source 244 to receive light along line 245. Light is detected by the photo cell 248 so long as the ball 236 floats in liquid present in the chamber 212. If the reservoir 256 empties and the level of aspirate in the chamber 212 falls, the ball 236 progressively descends to its lowest position 238, thereby interrupting the transmission of light from the light source 244 to the photo cell 248. The return of filtered aspirate is terminated whenever the ball 236 interrupts the light detected by the photo cell 248. To prevent inadvertent delivery of air should the pump control fail, further descent of ball 236 results in its seating in and occluding connection point 222 at position 238.

Figure 3:
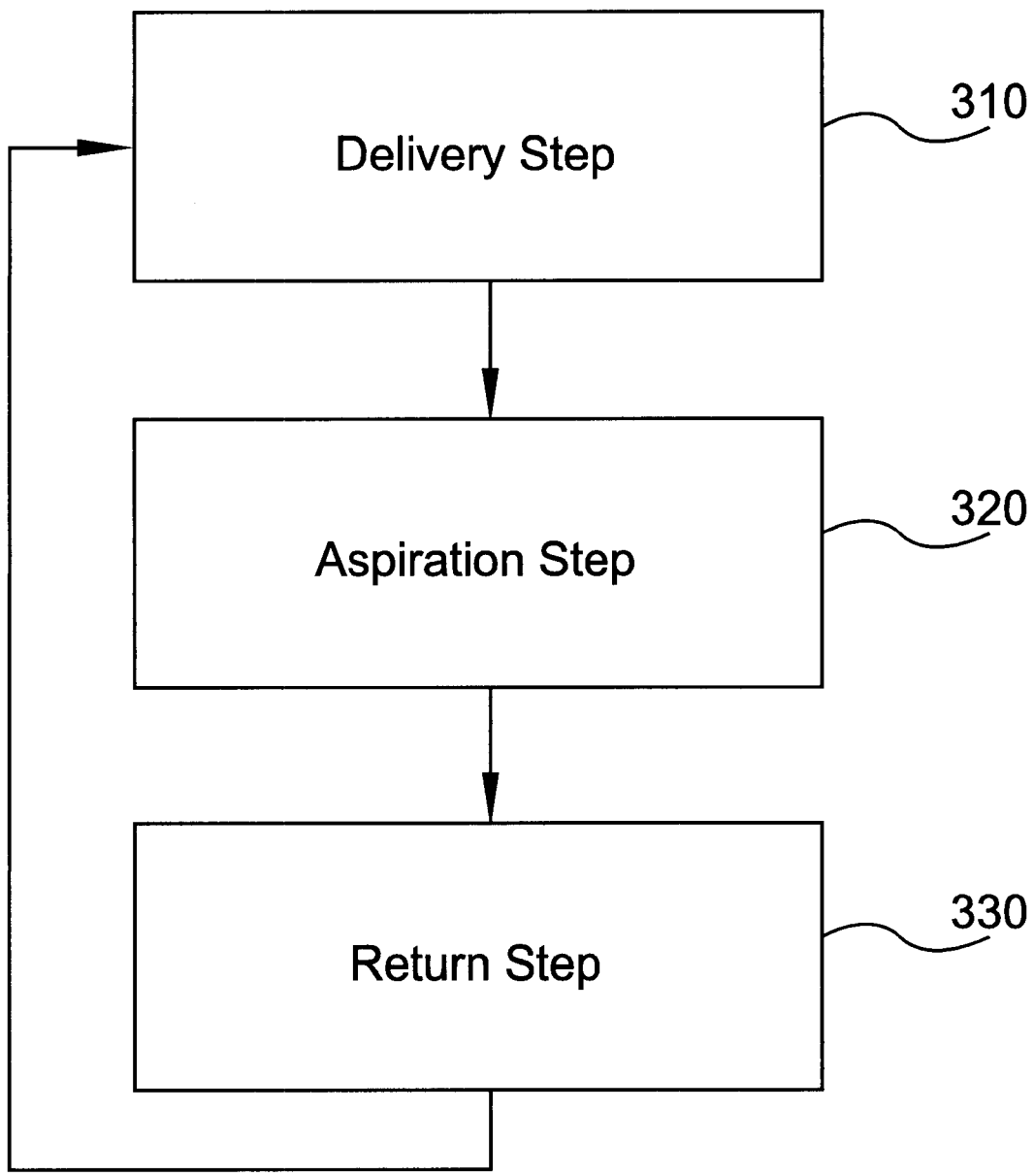
FIG. 3 is a flowchart representing the method of alternating aspiration and feeding in accordance with the present invention.

It should be further appreciated that the invention disclosed herein may also be characterized as a method of alternately (or simultaneously) delivering nutrition, fluids, medicine and/or aspirate to the gastro-intestinal tract and aspirating the gastrointestinal tract using feeding and aspiration tube(s) properly placed within a patient's gastrointestinal tract. This method 300 is illustrated more fully in FIG. 3. Roughly speaking, this method 300 comprises three distinct steps. During the delivery step 310 nutrition, fluids, and/or medicine ("feeding") is delivered via a feeding tube to the gastro-intestinal tract. During the aspiration step 320 material within a more proximal segment of the gastrointestinal tract is aspirated via an aspiration tube. During the return step 330 material aspirated from the gastro-intestinal tract is returned. In its broadest conception, these three steps may be conducted in any order, or even simultaneously, and may utilize more than one tube.

Figure 4:
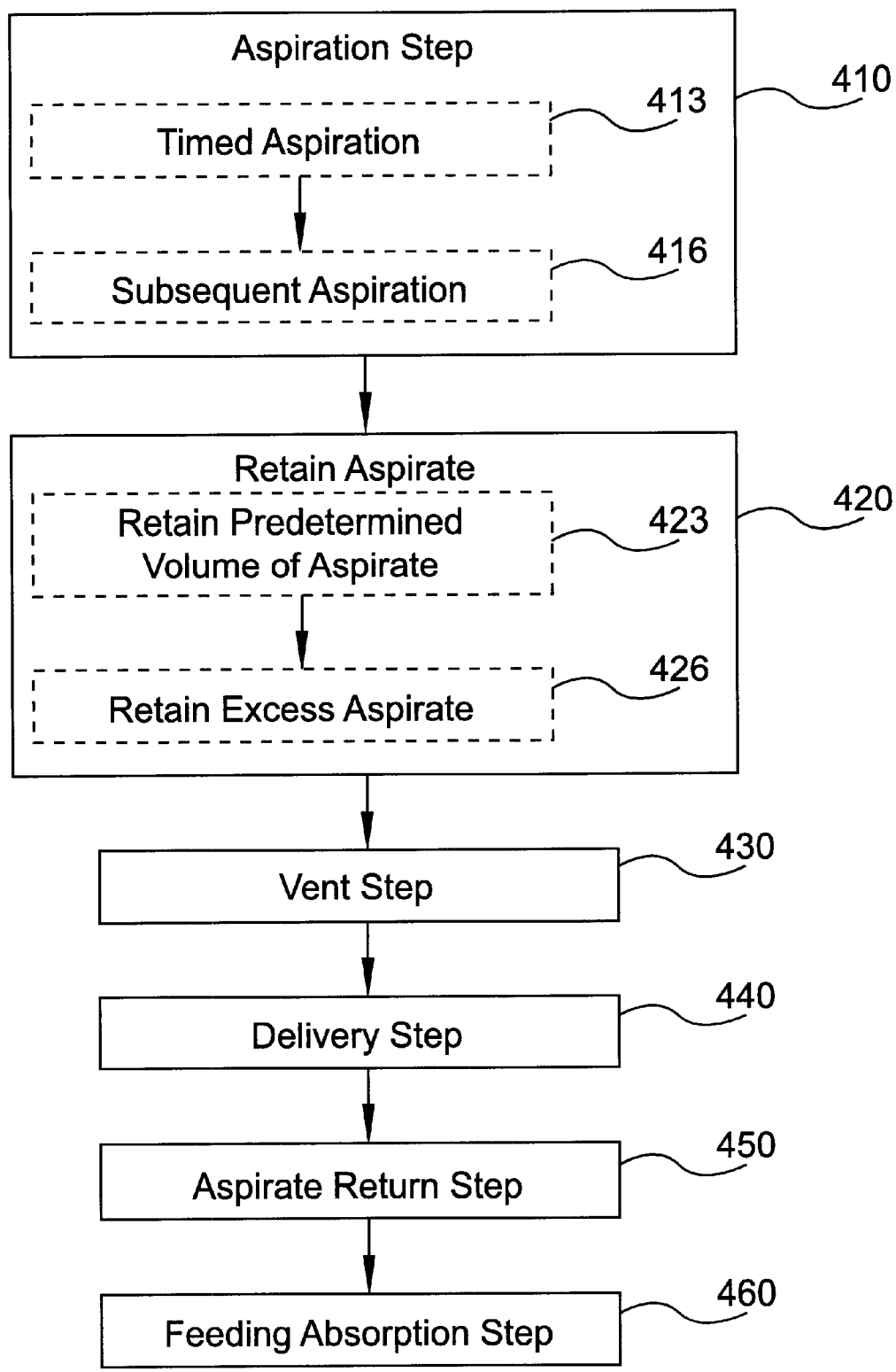
FIG. 4 is a flowchart representing the method of processing aspirate for cyclical return with feeding of nutrition in accordance with the preferred embodiment of the present invention.

A more detailed method in accordance with the preferred embodiment of the present invention is illustrated in FIG. 4. The method 400 provides for the delivery of nutrition, fluids, medicine and/or aspirate and the aspiration of the gastrointestinal tract utilizing a single lumen tube. The pump control apparatus 100 in accordance with the preferred embodiment of the present invention illustrated in FIG. 1 is particularly suited for use in accordance with method 400.

The aspiration step 410 aspirates air and excessive fluids from the gastro-intestinal tract. The aspiration step 410 may comprise discreet sub-steps of an initial timed aspiration 413 and a continuing aspiration 416. During the timed aspiration 413 aspiration is performed for a pre-determined period, such as ten seconds. The subsequent aspiration 416 sub-step would continue until aspirate flow ceases. As described in conjunction with FIG. 1, a flow detector may be used to determine when aspirate flow ceases.

After the aspiration step 410, the aspirated material is held for subsequent return to the patient's gastro-intestinal tract in the retain aspirate step 420. The retain aspirate step 420 may compromise two sub-steps. In sub-step 423, a predetermined maximum volume of aspirate, such as 10 ml, is retained for return to the patient in a subsequent step of method 400. In sub-step 426, aspirate in excess of the predetermined volume of substep 423 is retained indefinitely for subsequent evaluation by medical personnel.

Any air aspirated from the gastro-intestinal tract during the aspiration step 410 is removed from the aspirated material during the vent step 430. As previously noted, the presence of air in the gastro-intestinal tract impairs intestinal function. The removal of air during the vent step 430 prevents air from being reintroduced to the gastro-intestinal tract during a subsequent step of method 400.

Next, nutrition, fluids, and/or medicine ("feeding") are delivered to the gastrointestinal tract during the delivery step 440. A physician will determine an appropriate rate of delivery, which may typically be one-half ml of nutrition per second for about three to eight seconds.

After the delivery step 440, the aspirate from sub-step 423 of the retain aspirate step 420 is returned to the gastro-intestinal tract during the aspirate return step 450. This return of aspirate avoids dehydration of the patient by preventing any net removal of his or her own secretions, and the inconvenience and expense of replacing liquid through intravenous infusions. The net effect of proximal aspiration and then return of aspirate into the more distal gastro-intestinal tract is a mechanical aid to propulsion, as previously aspirated fluids are transported down stream where absorption is more efficient.

The gastro-intestinal tract then is given an opportunity to absorb the nutrition and secretions during the feedings absorption step 460. During the feedings absorption step 460, no aspiration or delivery of material occurs. The feedings absorption step 460 may last from a few seconds to a minute, or even substantially longer if deemed appropriate by medical personnel. In some circumstances, it might likewise be desirable to drastically shorten or omit the feedings absorption step 460.

The method 400 thereafter returns to the aspirate step 410 and continues until terminated by medical personnel.

Of course, numerous possible variations to the apparatus and method disclosed herein exist which do not depart from the scope of the invention. For example, the steps of method 400 may be ordered differently, or discreet steps as described herein may be combined into single steps. The duration of particular steps and/or sub-steps may be varied significantly without departing from the spirit of the present invention. The nonocclusive heavy ball and upper chamber of the pump control apparatus may take different shapes and forms. Any flow detector could be used in place of the combination of the upper chamber, the non-occlusive heavy ball, the light source, and the photocell disclosed herein. Of course, the sizes and dimensions of components can be varied to meet the needs of a particular practitioner. As described more fully herein, multiple tubes may be used for aspiration and delivering nutrition. Also, separate pumps may optionally be used for aspiration and delivering nutrition. Additional variations will be apparent to one of ordinary skill in the art.

What is claimed is:

1. A method for the aspiration of the gastro-intestinal tract and delivery of nutrition, fluids, medicine and aspirate to the gastro-intestinal tract, the method comprising the steps of:
    placing a combination feeding and aspiration tube within the patient's gastro-intestinal tract;
    aspirating the gastro-intestinal tract using the combination feeding and aspiration tube;
    retaining aspirate for subsequent return to the patient's gastro-intestinal tract;
    venting air from the retained aspirate;
    delivering feeding into the gastro-intestinal tract using the combination feeding and aspiration tube; and
    returning retained aspirate to the gastro-intestinal tract.

2. The method of claim 1 further comprising the step of allowing the gastro-intestinal tract to absorb material without delivery of additional material.

3. The method of claim 2, wherein the step of aspirating further comprises the sub-steps of:
    aspirating the gastrointestinal tract for a predetermined time; and
    continuing aspiration of the gastro-intestinal tract until aspirate flow ceases.

4. A pump control apparatus for use with a combination feeding and aspiration tube, the apparatus comprising:
    a connection point adapted to be operably attached to a combination feeding and aspiration tube;
    a chamber joined to the connection point such that aspirated material passes from the combination feeding and aspiration tube, through the connection point, and through the chamber; and
    a flow detector to detect the flow of aspirate through the chamber.

5. The pump control apparatus of claim 4, further comprising:
    a switching mechanism operably connected to the flow detector so as to cease aspiration when the flow detector does not detect a flow of aspirate through the chamber.

6. The pump control apparatus of claim 5, further comprising a reservoir operatively joined to the chamber such that aspirate flows through the chamber and into the reservoir.

7. The pump control apparatus of claim 6, further comprising an overflow chamber positioned to receive any aspirate which overflows the reservoir.

8. The pump control apparatus of claim 7, further comprising a filter within the reservoir positioned such that aspirate must flow through the filter prior to being re-introduced into a patient's gastro-intestinal tract.

9. The pump control apparatus of claim 5, further comprising a lower chamber between the connection point and the chamber, such that aspirate may flow through the connection point, through the lower chamber, and into the chamber.

10. The pump control apparatus of claim 5, further comprising a light ball positioned in a free floating manner within the lower chamber, such that it rises when aspirate is present in the lower chamber and such that it seals against the connection point when no aspirate flows through the chamber, thereby venting the introduction of air through the connection point into the intestine.

11. The pump control apparatus of claim 4 wherein the flow detector comprises:
    a heavy ball positioned in a free floating manner within the chamber, such that it rises when aspirate flows through the chamber and drops when no aspirate flows through the chamber;
    a light source positioned outside of the chamber such that light is transmitted through the chamber; and
    a light detector positioned outside of the chamber substantially opposite from the light source such that the light detector receives light from the light source when the ball rises in an aspirate flow and such that the light source does not receive light from the light source when the ball drops in the absence of an aspirate flow.

12. The pump control apparatus of claim 11, wherein the flow detector comprises:
    a light source positioned so as to transmit light through the upper chamber;
    a photocell positioned so as to receive the light transmitted from the light source after the light has passed through the upper chamber; and
    a non-occlusive heavy ball free floating within the upper chamber such that the heavy ball rises within the upper chamber while liquid material is aspirated and drops within the upper chamber when liquid material is not aspirated the heavy ball positioned such that it will interrupt the light transmitted through the upper chamber as it rises and drops within the upper chamber.

13. The pump control apparatus of claim 11, further comprising a floating ball within the lower chamber designed so as to seat within the connection point when no fluid is present within the lower chamber.

14. A pump control apparatus of claim 11, further comprising an overflow chamber to receive fluid exceeding the capacity of the reservoir.

15. The pump control apparatus of claim 11, wherein the upper chamber comprises an hour glass shape, wherein the mid-section of the upper chamber is narrower than the lower portion or upper portion of the upper chamber.

16. A pump control apparatus for use with a combination feeding and aspiration tube, the apparatus comprising:

a connection point adapted to be operably attached to a combination feeding aspiration tube, the connection point configured to allow liquid material to flow there through;

a lower chamber operably connected to the connection point such that liquid material may pass between the lower chamber and the combination feeding and aspiration tube;

an upper chamber operably connected to the lower chamber such that liquid material may pass between the lower chamber and the upper chamber;

a reservoir operably connected to the upper chamber such that liquid material may pass between the upper chamber and the reservoirs;

a flow detector to detect aspirate flow through one of the chambers; and a pump operably connected to the connection point such that it alternatively aspirates through the tube and forces feedings through the tube, the direction of operation of the pump being controlled by the photocell as the light detected by the photocell is interrupted by the heavy ball.

* * * * *